(12) United States Patent
Holder et al.

(10) Patent No.: US 11,980,405 B2
(45) Date of Patent: May 14, 2024

(54) METHOD FOR TREATING FRACTURED VERTEBRAE

(71) Applicant: Joline GmbH & Co. KG, Hechingen (DE)

(72) Inventors: Bernd Holder, Balingen (DE); Michael Eisenlohr, Hechingen (DE); Peter Kohlbecher, Engen (DE); Uwe Furtwaengler, Bopfingen (DE)

(73) Assignee: Joline GmbH & Co. KG, Hechingen (DE)

( * ) Notice: Subject to any disclaimer, the term of this patent is extended or adjusted under 35 U.S.C. 154(b) by 933 days.

(21) Appl. No.: 16/856,248

(22) Filed: Apr. 23, 2020

(65) Prior Publication Data
US 2021/0330365 A1    Oct. 28, 2021

(51) Int. Cl.
| | |
|---|---|
| *A61B 17/88* | (2006.01) |
| *A61B 17/34* | (2006.01) |
| *A61B 17/56* | (2006.01) |
| *A61M 25/00* | (2006.01) |
| *A61M 25/01* | (2006.01) |

(52) U.S. Cl.
CPC ...... *A61B 17/8811* (2013.01); *A61B 17/3423* (2013.01); *A61B 2017/564* (2013.01); *A61B 17/8855* (2013.01); *A61M 2025/0008* (2013.01); *A61M 25/0102* (2013.01)

(58) Field of Classification Search
CPC . A61B 17/88; A61B 17/8802; A61B 17/8805; A61B 17/8808; A61B 17/8811; A61B 17/8816; A61B 17/8819; A61B 17/3423
See application file for complete search history.

(56) References Cited

U.S. PATENT DOCUMENTS

| | | | |
|---|---|---|---|
| 2014/0358188 A1* | 12/2014 | Larson | A61B 17/8819 606/86 R |
| 2015/0257809 A1* | 9/2015 | Schaus | A61B 17/8811 606/93 |
| 2016/0113690 A1* | 4/2016 | Sweeney | A61B 17/8861 606/279 |
| 2018/0228476 A1* | 8/2018 | Cannon | A61B 10/04 |

\* cited by examiner

*Primary Examiner* — Si Ming Ku
(74) *Attorney, Agent, or Firm* — Jason H. Vick; Sheridan Ross, PC

(57) ABSTRACT

The present invention concerns to a method, a percutaneous access path providing device and a kit of instruments for the treatment of fractured vertebrae, in particular for treating spinal compression fractures in humans. In particular the invention concerns to a percutaneous access path providing device comprising a vertebra access cannula and a vertebra introducer stylet, wherein the vertebra introducer stylet has a tip.

15 Claims, 7 Drawing Sheets

METHOD FOR TREATING FRACTURED VERTEBRAE

FIELD

One aspect generally relates to the treatment of fractured vertebrae, in particular for treating spinal compression fractures in humans.

BACKGROUND

In Germany, more than 30 million people suffer from bone-related illnesses, 7.8 million of them from osteoporosis. Demographic developments and lifestyle changes will contribute to an increase in the amount of people suffering from osteoporosis. Vertebral compression fractures are among the most common complications of osteoporosis. These occur not only as a result of falls, they can also be caused by everyday actions such as lifting a bag, bending over or even just sneezing. Osteoporosis is characterized by gradual loss or demineralization of spongy cancellous bone, causing the remaining bone to become brittle and lose elasticity, thus rendering the bone weaker and more prone to fracture. Where osteoporosis has significantly affected and/or unable to solely support the loads placed on the spine, and thus the vertebral bodies become especially prone to fracture.

Fractured vertebrae and loss of bone mass lead to changes in the posture. The person begins to lose height and often develops a curved back, the so-called dowager's hump. When their vertebrae collapse, people are more and more limited in their daily lives. They become less mobile and eventually need increasing the amount of painkillers.

The kyphoplasty is a minimally-invasive procedure that has been developed to access and treat diseased or fractured bone, such as collapsed or fractured vertebral bodies of individuals suffering from osteoporosis. This procedure requires a bilateral approach into vertebral structures. In a kyphoplasty procedure, a surgeon uses balloon catheter, wherein an expandable structure of the balloon catheter expands in the cancellous bone structure and create a void. Thereby the remaining cancellous bone structure is compacted, wherein the cortical bone structure of the weakened and/or fractured vertebral body is expanded. Then bone cement is injected into the void of a weakened and/or fractured bone in an attempt to reinforce the bone and prevent further weakening or fracture.

The recently kyphoplasty procedure can be divided in the following steps: (1) incising a skin portion; (2) introducing a percutaneous access path providing device for providing an access path to the vertebral body; (3) inserting a balloon catheter through an access cannula and into the vertebral body and getting gently inflated. As the balloon inflates, it compacts the soft cancellous bone to create a void inside the vertebral body and return the vertebral body to a natural height; and (4) removing the balloon catheter and filling the void gradually with bone cement.

This procedure employs a kit of different instruments. First, a straight, rigid vertebra access cannula having an inner lumen through which the interior of the vertebral body is accessed is needed. Consequently, the size of the inner lumen of such instrument basically defines the maximum dimensions of any other surgical tool that can pass through the vertebra access cannula into the vertebral body. The cannula has preferably a small diameter therefore very little soft tissue and/or bone trauma is caused. The smaller access path allows the instruments to be inserted through the pedicles in the vertebral bodies of the thoracic and lumbar regions of the human spine. The disadvantage of a too small diameter is that the simple injection of filler necessitates use of higher pressures, which can cause damage or an uncontrollable leakage of cement to a non-targeted, vital structure such as a nerve or blood vessel.

To penetrate and get an access into the vertebral body an access device with a tip, called vertebra introducer stylet is also needed. This instrument is recently inserted in the vertebra access cannula and fixed therein. When using both the cannula and the stylet fixed together one method step in the kyphoplasty is eliminated, because with the insertion of both a percutaneous access path to the vertebral body is provided in only one step.

A kyphoplasty procedure, however, has some disadvantages; the instruments that currently exist have not been fully adapted to meet the needs of patients. In an effort to solve these problems, other inventions have sought different instruments e.g. new balloon catheter or filling instruments for filling the bone cement into the vertebrae body. However, the disadvantage is that there are only a few developments on the vertebra introducer stylets. However, this instrument is one of the most important instruments in the kyphoplasty because it provides the percutaneous access path to the vertebra body. Currently there are just a few different types and styles of handheld surgical instruments that surgeons use to gain access into interior body regions. These instruments are intended to penetrate tissue by the application of pushing force, twisting force, or both in combination.

When using a vertebra introducer stylet, which is guided, e.g. using a tamping tool, through the inner lumen of the vertebra access cannula, as a cutting implement/cutting set, there is a risk of causing tissue or bone fracture, in which may lead to tissue injury or bone fragments, which in turn can injure the blood and nerve vessels. This is because the percutaneous access path providing device may hit into the bone by the surgeon using a surgical hammer. The currently common used vertebra introducer stylet tips have different numbers of symmetrical cut surfaces. Presently there exist tips with one (bevel tip), two (diamond tip) or three symmetrical cut surfaces. These tips have the disadvantages described above. Therefore new vertebra introducer stylets are needed.

These disadvantages and shortcomings of the prior art are presented for the reader's understanding only. This disclosure is not meant to limit the present invention in any way. Other features and advantages of the present invention are set forth and will become apparent in the following description and drawings, as well as in the appended claims.

SUMMARY

Against this background, it is an aspect of the invention to provide a method, a percutaneous access path providing device and a kit of instruments for the treatment of fractured vertebrae, in particular for treating spinal compression fractures in humans, which overcomes the problems of the instruments and methods of the state of the art. The present invention desirably permits surgeons an extrapedicular or transpedicular approach into vertebral bodies as they prepare that bone for treatment. Whether a transpedicular or extrapedicular approach is selected will depend on the patient's anatomy and the treatment sought.

The percutaneous access path providing device of the present invention comprises a vertebra access cannula and a vertebra introducer stylet. The vertebra introducer stylet is inserted into/guided through the inner lumen of the vertebra access cannula and is used as a tissue and bone access instrument and as a cutting implement to guide and set the vertebra access cannula before being retracted. In one embodiment, the vertebra introducer stylet is longer than the vertebra access cannula.

The percutaneous access path providing device of the present invention is a surgical instrument that allows initial placement of both a vertebra access cannula and a vertebra introducer stylet into interior body regions, and allows for later withdrawal of the vertebra introducer stylet while leaving the vertebra access cannula in place. The invention obviates the need for several instruments during surgical procedures, and simplifies interior access protocol.

The vertebra access cannula serves as the access sheath between the outside environment and the interior of a bone, through which a surgeon may introduce implements and prepare bone in a desirable manner as it is readied for treatment. The provision of a percutaneous access path to the vertebral body is affected by the percutaneous access path providing device according to the present invention.

The vertebra access cannula according to the present invention has an elongated tubular body with an inner lumen, a proximal end and distal end and a longitudinal axis along the elongated tubular body, wherein the inner lumen extending the length of the elongated tubular body and has a substantially equal diameter along its longitudinal axis.

The vertebra introducer stylet according to the present invention has an elongated cylindrical body, a proximal end and distal end and a longitudinal axis along the elongated cylindrical body, wherein the elongated cylindrical body has a substantially equal diameter along its longitudinal axis, wherein the diameter of the elongated cylindrical body is less than the diameter of the inner lumen of the vertebra access cannula but nearly equal to the diameter of the inner lumen of the vertebra access cannula such that the vertebra introducer stylet fills the inner lumen of the vertebra access cannula but may be retracted through the inner lumen, and wherein the distal end terminates in a tip, wherein the tip is arranged eccentrically to the longitudinal axis of the elongated cylindrical body, wherein the tip is formed by three cut surfaces, wherein a first cut surface is larger than the second and third cut surfaces, wherein the second and third cut surfaces are identical in size.

It is an aspect of the present invention to allow a surgeon to prepare cancellous bone in a predictable and controlled manner. The present invention has as its objective the ability to achieve a transpedicular or extrapedicular approach with a lower risk of causing tissue injury or bone fracture while the procedure by the surgeon because of the eccentrically arranged tip of the vertebra introducer stylet. As a further objective, the present invention seeks to speed up the procedure of the kyphoplasty by merging individual method steps and reduces the number of required instruments and therefore saves costs.

As a further objective, the present invention seeks to provide a kit with all essential instruments needed for a save and smooth kyphoplasty surgery. This kit comprises the above described percutaneous access path providing device.

A further aspect of the invention provides a method for treating fractured vertebrae of patient in need thereof, wherein the method provides a percutaneous access path providing device adapted for insertion through soft tissue to a target bone treatment site.

The foregoing has outlined, in general, the physical aspects of the invention and serves as an aid to better understand the more complete detailed description which follows. In reference to such, there is to be a clear understanding that the present invention is not limited to the method or detail of construction, fabrication, material, or application of use described and illustrated herein. Any other variation of fabrication, use, or application should be considered apparent as an alternative embodiment of the present invention.

It will be appreciated that the aforementioned features and those still to be explained below can be used not only in the respectively cited combination but also in other combinations or on their own, without departing from the scope of the present invention.

Features and advantages of the various aspects of the invention are set forth in the following Description and Drawings, as well as in the appended Claims.

BRIEF DESCRIPTION OF THE DRAWINGS

The following drawings serve to illustrate the various aspects of the invention. These drawings further describe by illustration, the advantages and aspects of the present invention. Each drawing is referenced by corresponding figure reference characters within the "DESCRIPTION OF PREFERRED EMBODIMENTS" section to follow.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF PREFERRED EMBODIMENTS

The present invention allows a surgeon to treat fractured vertebrae of a patient in need thereof predictably, and in a controlled manner. By employing the aspects of the present invention, a surgeon can access the interior of a bone and treat fractured vertebrae. The present invention gives a surgeon an instrument with which to minimize damage to a vertebral body and surrounding tissues but optimize preparation options.

Although the disclosure hereof is detailed to enable those skilled in the art to practice the invention, the physical embodiments herein disclosed merely exemplify the invention that may be embodied in other specific structures. Although the preferred embodiment is described, the details may be changed without departing from the invention.

Figure 1:
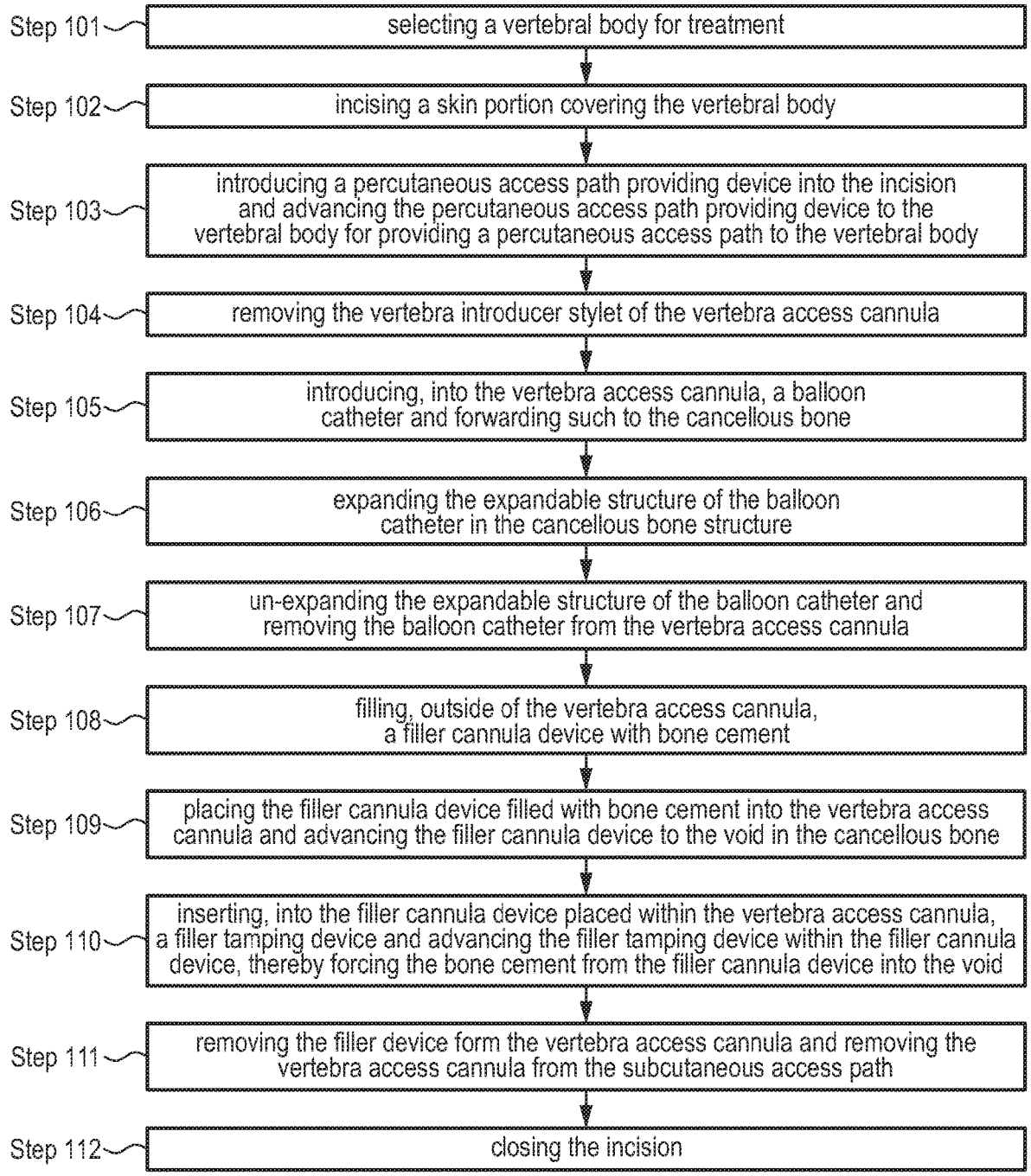
FIG. 1 depicts a flowchart of a first method version of the treatment of fractured vertebrae of a patient according to embodiments of the invention.
Figure 2:
FIG. 2 depicts a flowchart of a second method version of the treatment of fractured vertebrae of a patient according to embodiments of the invention.

The method 100 and 200 for treating fractured vertebrae of a patient in need thereof according to the present invention is illustrated in FIGS. 1-2. The percutaneous access path providing device 300 for advancing to the vertebral body for providing a percutaneous access path to the vertebral body with its vertebra access cannula 400 and vertebra introducer stylet 500 according to the present invention is illustrated in FIGS. 3-6. The kit 600 for treating fractured vertebrae of a patient in need thereof according to the present invention is illustrated in FIG. 7.

FIG. 1 demonstrates the method 100 according to the invention, wherein the method 100 comprising the twelve consecutive steps 101-112. According to an embodiment of the invention the method 100 can be extended by further process steps. According to another embodiment of the invention the method 100 may be performed with the instruments shown in the kit 600 of FIG. 7 for treating fractured vertebrae. This is because these instruments can be advantageously used for this purpose.

In a typical surgical procedure, a patient lies on an operating table, while the physician introduces the different instruments into soft tissue in the patient's back. The patient can lie face down on the table, or on either side, or at an oblique angle, depending upon the physician's preference. Moreover, the procedure can be performed through a percutaneous posterior procedure. Therefore the first step 101 of the method 100 is selecting a vertebral body for treatment, the vertebral body comprising a fracture and having an outer cortical bone structure, an inner cancellous bone structure surrounded by the outer cortical bone structure, and two pedicles.

In a next step 102 the surgeon incises a skin portion covering the vertebral body for treatment to provide for an incision in the skin portion. According to an embodiment of the invention the incisions have a length of between about 0.5 and 3 cm.

According to another embodiment of the invention the method steps 102-112 are performed on each of the pedicle of the vertebral body with a separate set of devices, respectively, therefore in step 102 two incisions in the skin portion are provided (see method 200 shown in FIG. 2).

In a next step 103 of the method 100 according to the invention the surgeon introduces a percutaneous access path providing device 300 (shown in FIGS. 3-6) into the incision and advancing the percutaneous access path providing device 300 to the vertebral body for providing a percutaneous access path to the vertebral body. This step 103 may be performed under radiologic or CT monitoring. Therefore the surgeon advances the percutaneous access path providing device 300 through the soft tissue down and into the fractured vertebrae. According to an embodiment of the method step 103 the physician may use a surgical hammer for providing a percutaneous access path to the vertebral body.

The percutaneous access path providing device 300 comprises a vertebra access cannula 400 and a vertebra introducer stylet 500 (shown in FIGS. 3-6). The vertebra introducer stylet 500 is inserted in the vertebra access cannula 400. Therefore in step 103 both the distal ends 404 and 503 of the vertebra introducer stylet 500 and the vertebra access cannula 400 penetrate the soft tissue and cortical bone and the cancellous bone of the fractured vertebrae.

Preferably the depth of penetration of the distal ends 404 and 503 of the vertebra introducer stylet 500 and the vertebra access cannula 400 are through a first wall of the cortical bone and into the cancellous bone. However, if the penetration through the first wall of the cortical bone and into the cancellous bone is not achievable by manual advancement of the percutaneous access path providing device 300, a physician can continue penetration by gently striking the proximal ends 403 and 502 of the vertebra introducer stylet 500 and the vertebra access cannula 400 with a blunt instrument such as a surgical hammer.

After penetrating the cortical bone structure and the cancellous bone structure of the vertebral body the physician continues with step 104 by removing the vertebra introducer stylet 500 of the vertebra access cannula 400. Therefore the vertebra introducer stylet 500 is withdrawn from the vertebra access cannula 400 by surgeon such that the vertebra access cannula 400 remains within the cortical bone and allowing access to the passage formed in the interior of the vertebral body through the vertebra access cannula 400.

According to an embodiment of the invention the surgeon may use a bone drill 609 after method step 104. Therefore the physician advances a bone drill device 609 through the vertebra access cannula 400 and operating such, that a path is generated through the outer cortical bone structure into the inner cancellous bone structure. With other words the bone drill device 609 can be used to create a working channel in the vertebra. After the physician advances the bone drill device 609 through the vertebra access cannula 400 under X-ray control or using another external visualizing system the bone drill device 609 is removed the from the vertebra access cannula 400.

At this point in the procedure, access to the cancellous bone has been accomplished and distal end 404 of the vertebra access cannula 400 extends into the interior volume of the vertebral body, leaving only the vertebra access cannula 400 in place.

According to an embodiment of the invention the physician can now decide if a biopsy to obtain samples of cancellous bone or to harvest bone marrow is required. Therefore a vertebra biopsy device 608 can be used, wherein the vertebra biopsy device 608 is carried through the vertebra access cannula 400 into the interior volume of the vertebral body. The biopsy is preferably carried out under radiographic control. Alternatively or additionally, the physician can further use instruments for introducing medication or the like into cancellous bone.

In a next step 105 of the method 100 the physician now introduces a balloon catheter 601 into the vertebra access cannula 400 and forwarding such to the cancellous bone.

The balloon catheter 601 (shown in FIG. 7 as a part of the kit 600) is shaped and dimensioned to be insertable into the vertebra access cannula 400. The balloon catheter 601 has a first end and a second end, the first end being adapted for getting inserted into the vertebra access cannula 400 and the second end being adapted for remaining outside of the vertebra access cannula 400, the first end comprising an expandable balloon structure adapted to undergo expansion in the cancellous bone structure to a predetermined size and shape, the second end comprising adaptor means for connecting the balloon catheter 601 to a fluid providing means 602.

Preferably the expandable balloon structure has a length of 10, 16 or 22 mm, wherein the diameter is preferably 16 mm. Therefore the expandable balloon structure has a volume of about 3, 4 or 6 ml.

According to an embodiment the balloon catheter 601 comprises two different expandable structures, a first expandable structure 601a and a second expandable structure 601b, adapted to undergo expansion in the cancellous bone structure independently from one another, e.g. by means of a fluid to be guided into the structures 601a, 601b for this purpose. The two expandable structures 0601a, 601b can be inflated and deflated separately from one another. According to this embodiment the balloon catheter 601 is a double balloon catheter. With this embodiment each single balloon can be adjusted separately, because the pressure and volume amount is separately controllable. In case the surgeon provides two access paths, the double balloon technology provides the surgeon with four instead of two balloons per vertebra to restore vertebral height of the fractured vertebra. This allows for significantly increased control of the vertebral restoration and for detailed reconstruction of the fractured vertebral body even in its edge regions. Especially in difficult situations, this feature simplifies the procedure and offers additional treatment options. For instance, it is possible to fix the proximal balloons in the harder cortical bone behind the pedicle isthmus to first use the distal balloons for vertebral height restoration, thus preventing the phenomenon of the device taking the path of least resistance. The double balloon allows for independent control of four balloons inserted via a bipedicular approach, thus allowing for precise restoration of the vertebra even in more complex fractures.

According to another embodiment the balloon catheter 601 comprises marking rings at its distal end. Preferably the balloon catheter 601 comprises two or three marking rings immediately before and after or between the expandable structures/balloons. The marking rings on the catheter shaft indicate the position of the balloon catheter 601 in the vertebra introducer cannula 400 and in the vertebral body. The distal ring indicates that the balloon tip is exiting the vertebra introducer cannula 400. The middle ring indicates that the distal balloon is positioned in the vertebral body. When the proximal ring disappears in the vertebra introducer cannula 400, also the proximal balloon is positioned in the vertebral body. This special manufacturing technology prevents the balloons from expanding beyond their specified length.

After the surgeon introduces the balloon catheter 601 into the vertebra access cannula 400 in method step 105 the method step 106 of expanding the expandable structure in the cancellous bone structure to a predetermined shape and size to create a void in the cancellous bone, by providing fluid into the expandable structure via the fluid providing means 602 follows. In other words the cancellous bone is compacted to form a cavity in the vertebral body.

According to an embodiment the fluid, which is used to expand the expandable structure of the balloon catheter 601 in the cancellous bone structure is a contrast agent fluid. This has the advantage, that the expanded structure of the balloon catheter 601 is visible under X-ray control.

After the cancellous bone is compacted method step 107 of unexpanding the expandable structure and removing the balloon catheter 601 from the vertebra access cannula 400 follows. After this method step 107 again only the vertebra access cannula 400 extends into the interior volume of the vertebral body.

The next step 108 is performed outside of the vertebra access cannula 400. Therefore a filler cannula device 604 is filled with bone cement. In a next step 109 the filler cannula device 604 filled with bone cement is placed into the vertebra access cannula 400 and advancing the filler cannula device 604 to the void in the cancellous bone. In a following step 110 a filler tamping device 605 is inserted into the filler cannula 604 device placed within the vertebra access cannula 400 and the filler tamping device 605 within the filler cannula device 604 is advanced thereby the bone cement is forced from the filler cannula device 604 into the void. The filler cannula device 604 and the filler tamping device 605, nested together, forming a filler device 603.

When the physician is satisfied that the bone cement has been amply distributed inside the void in the cancellous bone the next step 111 is followed. Thereby, the filler cannula device 604 is removed form the vertebra access cannula 400 and the vertebra access cannula 400 is removed from the subcutaneous access path.

The use of a filler cannula device 604 in combination with a filler tamping device 605 offers significant benefits over cement syringes which may, due to differences in pressure, show some residual cement flow. Furthermore, the chance of overfilling and leakage of material outside the cavity portion is thereby significantly reduced.

According to an embodiment of the invention the filler cannula device 604 has an interior volume of about 1.5 ml. Therefore about 1.5 ml cement per cannula can be filled into the void of the vertebral body.

According to another embodiment of the invention the filler cannula device 604 comprises a first end and a second end, wherein the first end comprises a handle and is adapted to remain outside the vertebra access cannula 400, and wherein the second end comprises a side wall and a tip. According to this embodiment the second end may further comprises an opening, which is provided in the tip or in the side wall. This side opening allows a directional cement application.

According to an embodiment of the invention the filler tamping device 605 is flexible. Therefore, the filler tamping device 605 can easily be bent aside while using.

According to an embodiment of the invention the method steps 108, 109 and 110 are repeated in order to provide for a sufficient amount of bone cement into the void.

As a last step 112 of the method 100 the incision is closed by a surgeon According to an embodiment of the invention the vertebra access cannula 400, the vertebra introducer stylet 500, the balloon catheter 601, and/or the filler device 603 comprise markings. This embodiment has the advantage, that the instruments are visible under X-ray control.

According to another embodiment of the invention vertebra access cannula 400, the vertebra introducer stylet 500, the balloon catheter 601, and/or the filler device 603 comprise handles.

Of course, the method 100 could be repeated to access and treat one vertebral body multiple times in multiple orientations to create multiple voids in the cancellous bone that may or may not interconnect. After a void has been filled in the above described manner, the instruments can be withdrawn and the incision sites sutured closed. The bone treatment procedure is concluded. This embodiment of a second method version of the treatment of fractured vertebrae of a patient according to the invention is depicted in a flowchart in FIG. 2 by method 200. Therefore the steps 102-112 are performed on each of the pedicle of the vertebral body with a separate set of devices, respectively. Therefore in step 202 two incisions in the skin portion are provided, and after step 204 the method comprises the further consecutive steps of: 204a introducing, outside of the first vertebra access cannula 400, the vertebra introducer stylet 500 into a second vertebra access cannula 400, wherein the second vertebra access cannula 400 is identically structured as the first vertebra access cannula 400, wherein the second vertebra access cannula 400 and the vertebra introducer stylet 500, nested together, forming a second percutaneous access path providing device 300, 204b introducing the second percutaneous access path providing device 300 into the second incision and advancing the second percutaneous access path providing device 300 to the vertebral body for providing a second percutaneous access path to the vertebral body, and 204c removing the vertebra introducer stylet 500 of the second vertebra access cannula 400.

Figure 3A:
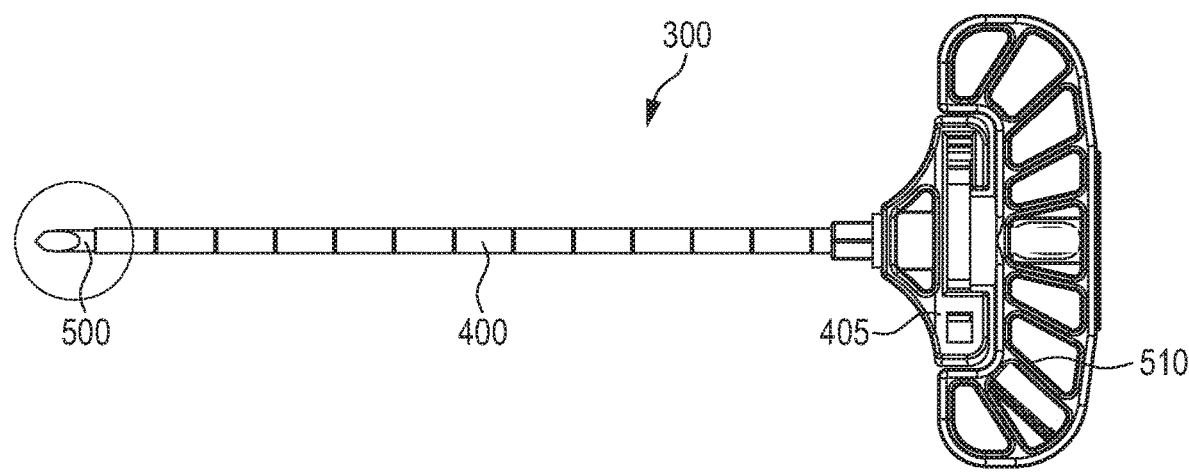
FIG. 3A depicts a perspective front side view of the percutaneous access path providing device, wherein the vertebra introducer stylet is inserted into the vertebra access cannula.

FIG. 3A shows a percutaneous access path providing device 300 for advancing to the vertebral body for providing a percutaneous access path to the vertebral body. The percutaneous access path providing device 300 comprising a vertebra access cannula 400 and a vertebra introducer stylet 500. The vertebra introducer stylet 500 is thereby inserted in the vertebra access cannula 400.

Figure 4A:
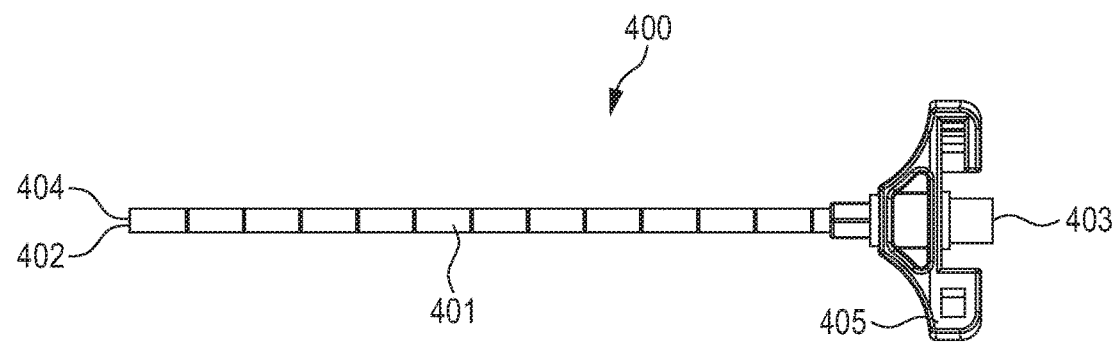
FIG. 4A depicts a perspective front side view of the vertebra access cannula, wherein the vertebra access cannula has a handle at the proximal end.
Figure 4B:
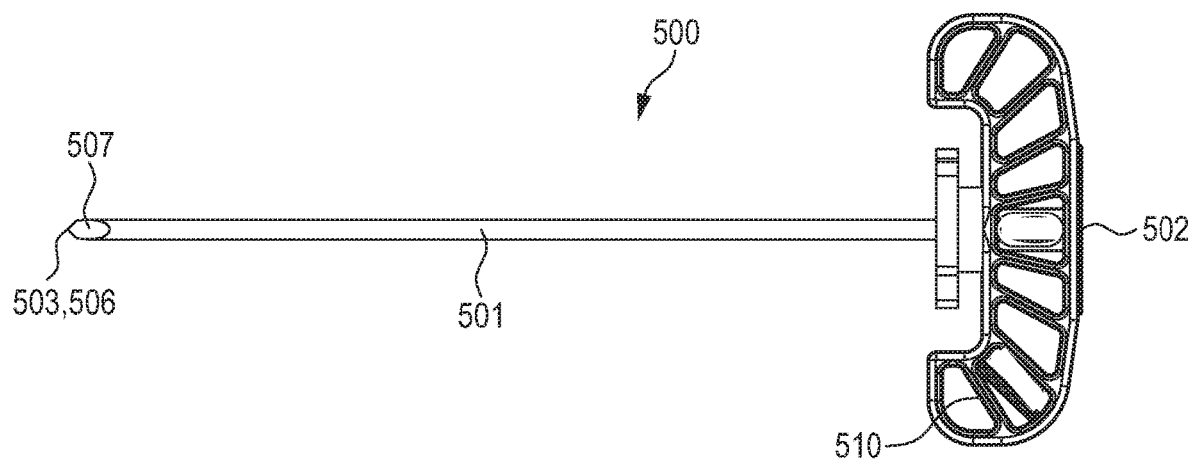
FIG. 4B depicts a perspective front side view of the vertebra introducer stylet, wherein the vertebra introducer stylet has a handle at the proximal end.

The vertebra access cannula 400 is shown in more detail and separately in FIG. 4A. The vertebra access cannula 400 has an elongated tubular body 401 with an inner lumen 402, a proximal end 403 and distal end 404 and a longitudinal axis along the elongated tubular body 401, wherein the inner lumen 402 extending the length of the elongated tubular body 401 and has a substantially equal diameter along its longitudinal axis. In other words the vertebra access cannula 400 has a desirably somewhat larger diameter and is not as long as the vertebra introducer stylet 500. As best shown in FIG. 3A, the access cannula 400 includes an inner lumen 402 that extends through the instrument from its distal end 404 to its proximal end 403. The inner lumen 402 is sized to accept the vertebra introducer stylet 500 to slide and/or rotate relative to the vertebra access cannula 400.

Referring to FIGS. 4B-6D the vertebra introducer stylet 500 functions as an instrument to penetrate tissue and bone. The vertebra introducer stylet 500 has an elongated cylindrical body 501, a proximal end 502 and distal end 503 and a longitudinal axis 504 along the elongated cylindrical body 501, wherein the elongated cylindrical body 501 has a substantially equal diameter 505 along its longitudinal axis 504, wherein the diameter 505 of the elongated cylindrical body 501 is less than the diameter of the inner lumen 402 of the vertebra access cannula 400 but nearly equal to the diameter of the inner lumen 402 of the vertebra access cannula 400 such that the vertebra introducer stylet 500 fills the inner lumen 402 of the vertebra introducer cannula 400 but may be retracted through the inner lumen 402, and wherein the distal end 503 terminates in a tip 506, wherein the tip 506 is arranged eccentrically to the longitudinal axis 504 of the elongated cylindrical body 501, wherein the tip 506 is formed by three cut surfaces 507, 508 and 509, wherein a first cut surface 507 is larger than the second and third cut surfaces 508 and 509, wherein the second and third cut surfaces 508 and 509 are identical in size.

According to an embodiment of the invention the vertebra access cannula 400 and a vertebra introducer stylet 500 comprise handles 405 and 510 at their proximal ends 403 and 502 as shown in FIGS. 3A, 4A, 4B and 5A. The handles 405 and 510 are arranged in such they can be fixed together by turning them against to each other. Furthermore, the handle 405 is designed smaller than the handle 510 such that the handle 405 is kept in the larger handle 510 (shown in FIG. 3A). The handles 405 and 510 fixed together aids a physician in manipulating the instrument 300, but a physician can also desirably use the handle 405 to independently manipulate the instrument 400 or the handle 510 to independently manipulate the instrument 500 during use.

Figure 5A:
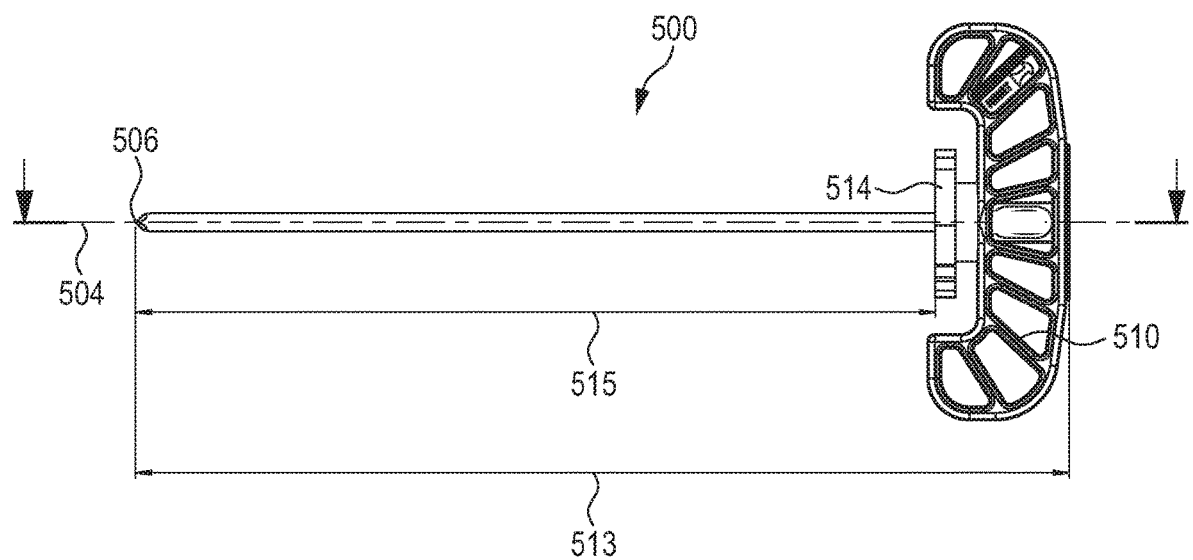
FIG. 5A depicts a perspective back side view of the vertebra introducer stylet shown in FIG. 4B, wherein the vertebra introducer stylet has a handle at the proximal end.
Figure 6A:
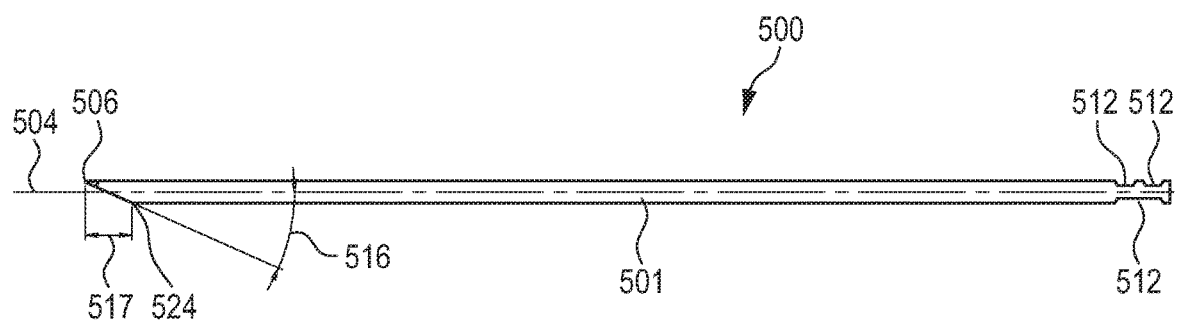
FIG. 6A depicts a perspective side view of the vertebra introducer stylet.

According to a further embodiment of the invention the vertebra introducer stylet 500 comprises a handle 510 at the proximal end 502, wherein the elongated cylindrical body 501 of the vertebra introducer stylet 500 has a length 513 including the handle 510 from the tip 506 to the handle 510 of 177.60 mm to 179.60 mm, preferably a length of 178.10 mm to 179.10 mm, more preferably a length of 178.60 mm (shown in FIG. 5A).

Figure 5B:
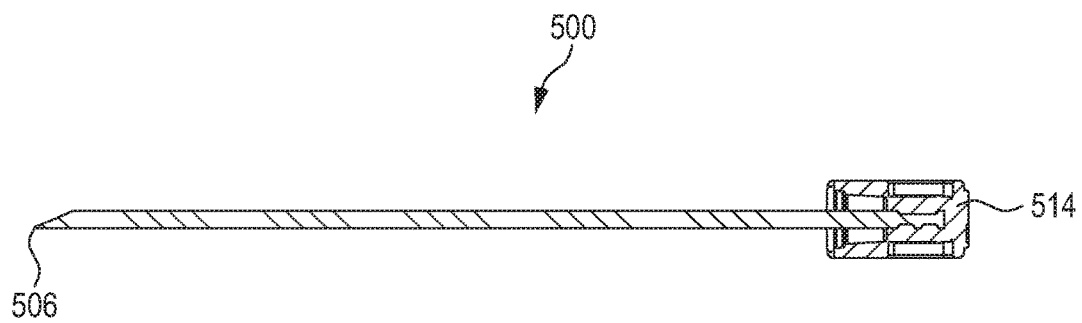
FIG. 5B depicts a perspective side view of the vertebra introducer stylet, wherein the proximal end of the vertebra introducer stylet is arranged in a stopper device.

Referring to FIGS. 5A and 5B the proximal end 502 of the elongated cylindrical body 501 of the vertebra introducer stylet 500 is arranged in a stopper device 514, wherein the elongated cylindrical body 501 of the vertebra introducer stylet 500 has a length 515 without the stopper device 514 from the tip 506 to the stopper device 514 of 152.00 mm to 154.00 mm, preferably a length of 152.50 mm to 153.50 mm, more preferably a length of 153.00 mm.

Figure 3B:
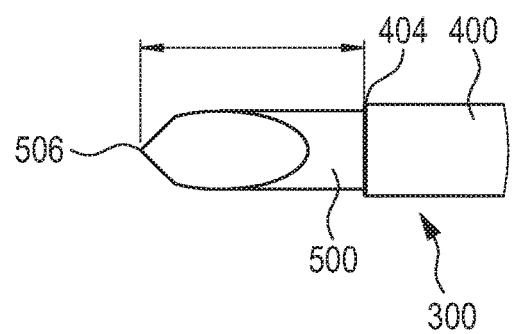
FIG. 3B depicts an enlarged perspective front side view of the distal end of the percutaneous access path providing device shown in FIG. 3A.

According to a preferred embodiment of the invention the elongated cylindrical body 501 of the vertebra introducer stylet 500 is longer than the elongated tubular body 401 of the vertebra access cannula 400, such that the vertebra introducer stylet 500 protrudes from the inner lumen 402 of the vertebra access cannula 400 (shown in FIGS. 3A and 3B). According to another preferred embodiment of the invention the vertebra introducer stylet 500 when arranged in the vertebra access cannula 400 the tip 506 of the vertebra introducer stylet 500 protrudes 9.00 to 11.00 mm, preferably 9.50 to 10.50, more preferably 10.00 mm from the distal end 404 of the vertebra access cannula 400.

Figure 6B:
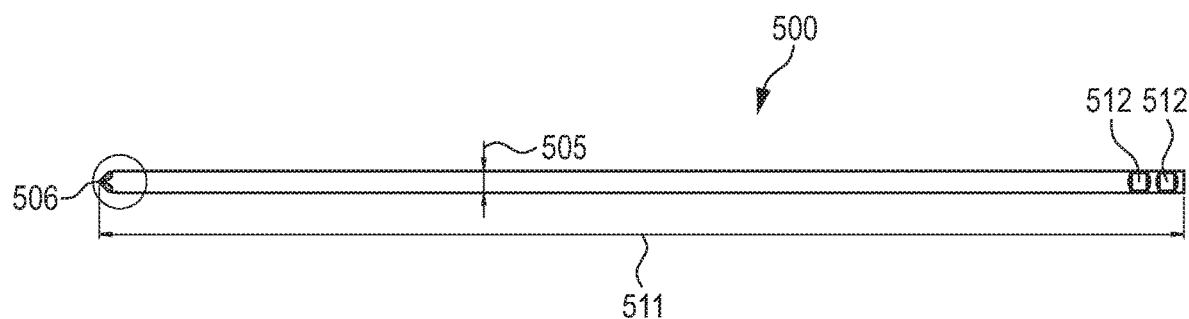
FIG. 6B depicts a perspective back side view of the vertebra introducer stylet shown in FIG. 6A.
Figure 7:
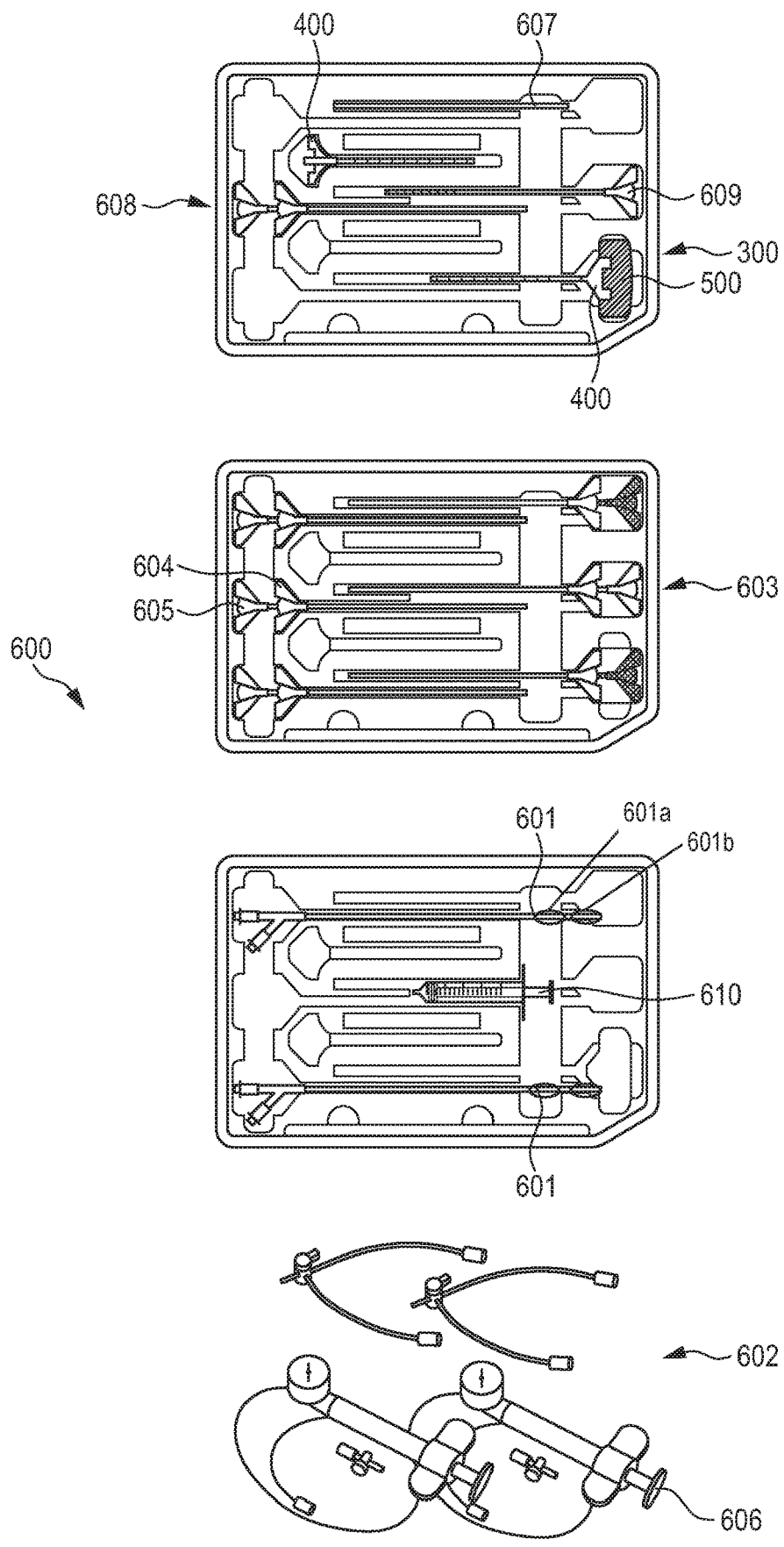
FIG. 7 depicts a perspective view of one version of a kit according to embodiments of the invention.

According to an embodiment of the invention the substantially equal diameter 505 of the elongated cylindrical body 501 of the vertebra introducer stylet 500 has a length of 3.40 mm to 3.60 mm, preferably a length of 3.45 mm to 3.55 mm, more preferably a length of 3.50 mm (shown in FIG. 6B).

According to an embodiment of the invention the elongated cylindrical body 501 of the vertebra introducer stylet 500 has a length 511 from the tip 506 to the proximal end 502 of 173.40 mm to 174.60 mm, preferably a length of 173.70 mm to 174.30 mm, more preferably a length of 174 mm (shown in FIG. 6B).

Referring to FIGS. 6A, 6B the elongated cylindrical body 501 of the vertebra introducer stylet 500 may have grooves 512 at its proximal end 502. These grooves 512 are advantageously for fixing a handle 510 at the proximal end 502.

According to an embodiment of the invention the first cut surface 507 of the tip 506 of the vertebra introducer stylet 500 is arranged in an angle 516 of 19 to 29° to the longitudinal axis 504 of the elongated cylindrical body 501, preferably in an angle 516 of 23 to 25°, more preferably in an angle 516 of 24° (shown in FIG. 6A).

According to another embodiment of the invention the first cut surface 507 of the tip 506 of the vertebra introducer stylet 500 has a length 517 from the tip 506 to an opposite end 524 of the first cut surface 507 of the tip 506 of 7.18 mm to 7.78 mm, preferably a length of 7.33 mm to 7.63 mm, more preferably a length of 7.48 mm (shown in FIG. 6A).

Figure 6C:
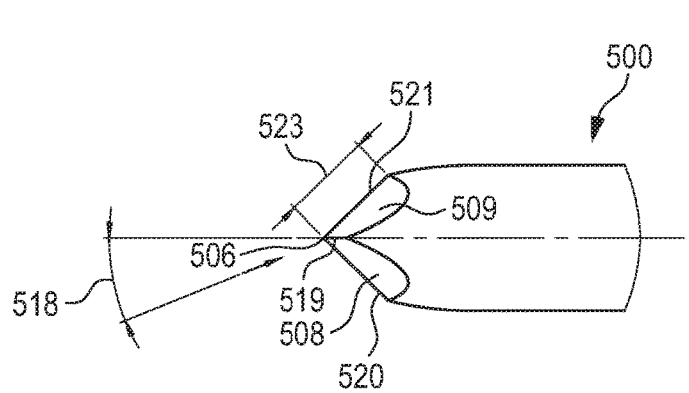
FIG. 6C depicts an enlarged perspective view of the tip of the vertebra introducer stylet of FIGS. 6A and 6B.

According to another embodiment of the invention the second and third cut surfaces 508 and 509 of the tip 506 of the vertebra introducer stylet 500 are arranged in an angle 518 of 17 to 27° to the longitudinal axis 504 of the elongated cylindrical body 501, preferably in an angle 518 of 21 to 23°, more preferably in an angle 518 of 22° (shown in FIG. 6C).

Figure 6D:
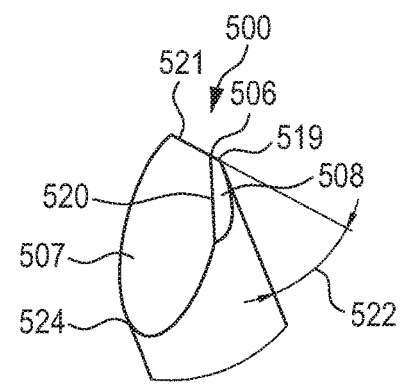
FIG. 6D depicts an enlarged a perspective view of the tip of the vertebra introducer stylet of FIGS. 6A and 6B.

According to another embodiment of the invention the tip 506 of the vertebra introducer stylet 500 is formed by three bevel 519, 520 and 521 wherein a first bevel 519 is shorter than the second and third bevel 520 and 521, wherein the second and third bevel 520 and 521 are identical in size, and wherein the first bevel 519 is arranged between the second and third cut surfaces 508 and 509 and wherein the first bevel 519 is arranged in an angle 522 of 35 to 45° from the tip 506 to the longitudinal axis 504 of the elongated cylindrical body 501, preferably in an angle 522 of 38 to 42°, more preferably in an angle 522 of 40° mm (shown in FIGS. 6C-6D). According to another embodiment of the invention the second and third bevel 520, 521 have a length 523 of 1.85 mm to 2.45 mm, preferably a length 523 of 2.00 mm to 2.30 mm, more preferably a length 523 of 2.15 mm.

A further aspect of the invention concerns to a kit 600 for treating fractured vertebrae of patient in need thereof. The kit 600 is shown in FIG. 7. The kit 600 comprises a percutaneous access path providing device 300, wherein the percutaneous access path providing device 300 comprises a vertebra access cannula 400 and a vertebra introducer stylet 500; a balloon catheter 601; fluid providing means 602; filler device 603 shaped and dimensioned to be insertable into the vertebra access cannula 400, wherein the filler device 603 comprises a filler cannula device 604 for filling with bone cement, and a filler tamping device 605 shaped and dimensioned to be insertable into the filler cannula device 400 for forcing the bone cement from the filler cannula device 604 into the void of the cancellous bone.

According to another embodiment of the invention the fluid providing means 602 comprising an inflation device 606. The inflation device 606 is used to inflate the single or double balloons of the catheter 601. Thereby, preferably a pressure of 10 to 12 bar (145 to 174 psi) is used.

According to another embodiment of the invention the kit 600 further comprises a cannula plug device 607 shaped and dimensioned to be insertable into the vertebra access cannula 400 for preventing inadvertent blood drainage through the vertebra access cannula 400 or for preventing a cement leakage through the vertebra access cannula 400. This further allows for multi-level treatment without the need of instant cement application.

According to another embodiment of the invention the kit 600 further comprises a second vertebra access cannula 400 for providing a second percutaneous access path to the vertebral body.

According to another embodiment of the invention the kit 600 further comprises a vertebra biopsy device 608 for taking a biopsy sample from the inner cancellous bone. The vertebra biopsy device 608 preferably comprises a needle and a plunger.

According to another embodiment of the invention the kit 600 further comprises a bone drill 609 for generating a path through the outer cortical bone structure into the inner cancellous bone structure. The bone drill 609 has a distal end a proximal end. The bone drill 609 is intended in use to fit for sliding and rotational movement within the interior lumen of the vertebra access cannula 400. The distal end of the bone drill 609 desirably includes cutting edges. In use, the cutting edges are intended to penetrate hard tissue in response to rotation and longitudinal load forces applied at the proximal end of the bone drill 609. Desirably the diameter of the bone drill 609 is smaller than the inner lumen 402 of the vertebra access cannula 400, and the length is longer than the vertebra access cannula 400, such that the bone drill 609 can access tissue deeper than the vertebra access cannula 40 when the vertebra access cannula 40 is installed in a patient.

The kit 600 of the invention can either further comprises bone cement or can be used with separately provided bone cement. The bone cement may be a PMMA bone cement which is specifically designed for spine surgery. Therefore the bone cement may offer a short mixing time and a long working time with high initial cohesion to minimize the leakage risk.

According to another embodiment of the invention the kit 600 further comprises a vacuum syringe 610. The vacuum syringe 610 can be used to remove air form the single or double balloon of the balloon catheter 601 prior to use. Furthermore it can be used together with the biopsy device 608 for aspiration to a bone specimen from the vertebral body into the biopsy cannula.

The vertebra introducer stylet 500, the balloon catheter 601, the filler device 603, the filler cannula device 604, the filler tamping device 605, the cannula plug device 607, the vertebra biopsy device 608 and the bone drill 609 are all shaped and dimensioned to be insertable into the vertebra access cannula 400.

Accordingly, aspects of the current technology are directed toward:

A method for treating fractured vertebrae of a patient in need thereof, the method comprising the following consecutive steps:

a) selecting a vertebral body for treatment, the vertebral body comprising a fracture and having an outer cortical bone structure, an inner cancellous bone structure surrounded by the outer cortical bone structure, and two pedicles, b) incising a skin portion covering the vertebral body for treatment to provide for an incision in the skin portion, c) introducing a percutaneous access path providing device into the incision and advancing the percutaneous access path providing device to the vertebral body for providing a percutaneous access path to the vertebral body, wherein the percutaneous access path providing device comprising a vertebra access cannula having an elongated tubular body with an inner lumen, a proximal end and distal end and a longitudinal axis along the elongated tubular body, wherein the inner lumen extending the length of the elongated tubular body and has a substantially equal diameter along its longitudinal axis, and a vertebra introducer stylet inserted in the vertebra access cannula having an elongated cylindrical body, a proximal end and distal end and a longitudinal axis along the elongated cylindrical body, wherein the elongated cylindrical body has a substantially equal diameter along its longitudinal axis, wherein the diameter of the elongated cylindrical body is less than the diameter of the inner lumen of the vertebra access cannula but nearly equal to the diameter of the inner lumen of the vertebra access cannula such that the vertebra introducer stylet fills the inner lumen of the vertebra access cannula but may be retracted through the inner lumen, and wherein the distal end terminates in a tip, wherein the tip is arranged eccentrically to the longitudinal axis of the elongated cylindrical body, wherein the tip is formed by three cut surfaces, wherein a first cut surface is larger than the second and third cut surfaces, wherein the second and third cut surfaces are identical in size, d) removing the vertebra introducer stylet of the vertebra access cannula, e) introducing, into the vertebra access cannula, a balloon catheter shaped and dimensioned to be insertable into the vertebra access cannula, and forwarding such to the cancellous bone; the balloon catheter having a first end and a second end, the first end being adapted for getting inserted into the vertebra access cannula and the second end being adapted for remaining outside of the vertebra access cannula, the first end comprising two expandable balloon structures, a first expandable structure and a second expandable structure, adapted to undergo expansion in the cancellous bone structure to a predetermined size and shape, wherein the first expandable structure and the second expandable structure are spaced from one another and wherein the first and the second expandable structure can be inflated and deflated independently from one another to create a desired void in the cancellous bone; and the second end of the balloon catheter comprising adaptor means for connecting the balloon catheter to a fluid providing means, f) expanding the expandable structure in the cancellous bone structure to a predetermined shape and size to create a void in the cancellous bone, by providing fluid into the expandable structure via the fluid providing means, g) un-expanding the expandable structure and removing the balloon catheter from the vertebra access cannula, h) filling, outside of the vertebra access cannula, a filler cannula device with bone cement, i) placing the filler cannula device filled with bone cement into the vertebra access cannula and advancing the filler cannula device to the void in the cancellous bone, j) inserting, into the filler cannula device placed within the vertebra access cannula, a filler tamping device and advancing the filler tamping device within the filler cannula device, thereby forcing the bone cement from the filler cannula device into the void, the filler cannula device and the filler tamping device, nested together, forming a filler device, and k) removing the filler cannula device form the vertebra access cannula and removing the vertebra access cannula from the subcutaneous access path, and l) closing the incision.

Any of the above aspects, wherein the steps are performed on each of the pedicle of the vertebral body with a separate set of devices, respectively, therefore in step b) two incisions in the skin portion are provided, and after step d) the method comprises the further consecutive steps of:

d1) introducing, outside of the first vertebra access cannula, the vertebra introducer stylet into a second vertebra access cannula, wherein the second vertebra access cannula is identically structured as the first vertebra access cannula, wherein the second vertebra access cannula and the vertebra introducer stylet, nested together, forming a second percutaneous access path providing device, d2) introducing the second percutaneous access path providing device into the second incision and advancing the second percutaneous access path providing device to the vertebral body for providing a second percutaneous access path to the vertebral body, and d3) removing the vertebra introducer stylet of the second vertebra access cannula.

Any of the above aspects, wherein incising of a skin portion comprises making two incisions with a length of between about 0.5 and 3 cm.

Any of the above aspects, wherein the steps h) i) and j) are repeated in order to provide for a sufficient amount of bone cement into the void.

Any of the above aspects, wherein the fluid is a contrast agent fluid.

Any of the above aspects, wherein the filler tamping device is flexible.

Any of the above aspects, wherein the filler cannula device comprises a first end and a second end, wherein the first end comprises a handle and is adapted to remain outside the vertebra access cannula, and wherein the second end comprises a side wall and a tip.

Any of the above aspects, wherein the second end further comprises an opening, which is provided in the tip or in the side wall.

Any of the above aspects, wherein the vertebra access cannula, the vertebra introducer stylet, the balloon catheter, and/or the filler device comprise markings.

Any of the above aspects, wherein the vertebra access cannula, the vertebra introducer stylet, the balloon catheter, and/or the filler device comprise handles.

Any of the above aspects, wherein the substantially equal diameter of the elongated cylindrical body of the vertebra introducer stylet has length of 3.40 mm to 3.60 mm, preferably a length of 3.45 mm to 3.55 mm, more preferably a length of 3.50 mm.

Any of the above aspects, wherein the elongated cylindrical body of the vertebra introducer stylet has a length from the tip to the proximal end of 173.40 mm to 174.60 mm, preferably a length of 173.70 mm to 174.30 mm, more preferably a length of 174 mm.

Any of the above aspects, wherein the vertebra introducer stylet comprise a handle at the proximal end, wherein the elongated cylindrical body of the vertebra introducer stylet has a length including the handle from the tip to the handle of 177.60 mm to 179.60 mm, preferably a length of 178.10 mm to 179.10 mm, more preferably a length of 178.60 mm.

Any of the above aspects, wherein the proximal end of the elongated cylindrical body of the vertebra introducer stylet is arranged in a stopper device, wherein the elongated cylindrical body of the vertebra introducer stylet has a length without the stopper device from the tip to the stopper device of 152.00 mm to 154.00 mm, preferably a length of 152.50 mm to 153.50 mm, more preferably a length of 153.00 mm.

Any of the above aspects, wherein the vertebra introducer stylet when arranged in the vertebra access cannula the tip of the vertebra introducer stylet protrudes 9.00 to 11.00 mm, preferably 9.50 to 10.50, more preferably 10.00 mm from the distal end of the vertebra access cannula.

Any of the above aspects, wherein the first cut surface of the tip of the vertebra introducer stylet is arranged in an angle of 19 to 29° to the longitudinal axis of the elongated cylindrical body, preferably in an angle of 23 to 25°, more preferably in an angle of 24°.

Any of the above aspects, wherein the first cut surface of the tip of the vertebra introducer stylet has a length from the tip to an opposite end of the first cut surface of the tip of 7.18 mm to 7.78 mm, preferably a length of 7.33 mm to 7.63 mm, more preferably a length of 7.48 mm.

Any of the above aspects, wherein the second and third cut surfaces of the tip of the vertebra introducer stylet are arranged in an angle of 17 to 27° to the longitudinal axis of the elongated cylindrical body, preferably in an angle of 21 to 23°, more preferably in an angle of 22°.

Any of the above aspects, wherein the tip of the vertebra introducer stylet is formed by three bevel wherein a first bevel is shorter than the second and third bevel, wherein the second and third bevel are identical in size, and wherein the first bevel is arranged between the second and third cut surfaces and wherein the first bevel is arranged in an angle of 35 to 45° from the tip to the longitudinal axis of the elongated cylindrical body, preferably in an angle of 38 to 42°, more preferably in an angle of 40°.

Any of the above aspects, wherein the second and third bevel have a length of 1.85 mm to 2.45 mm, preferably a length of 2.00 mm to 2.30 mm, more preferably a length of 2.15 mm.

Any of the above aspects, wherein the method comprises between step d) and step e) the further consecutive steps of:

e1) advancing a bone drill device through the vertebra access cannula and operating such, that a path is generated through the outer cortical bone structure into the inner cancellous bone structure, and e2) removing the bone drill device from the vertebra access cannula.

A percutaneous access path providing device for advancing to the verbral body for providing a percutaneous access path to the vertebral body, wherein the percutaneous access path providing device comprising:

a vertebra access cannula having an elongated tubular body with an inner lumen, a proximal end and distal end and a longitudinal axis along the elongated tubular body, wherein the inner lumen extending the length of the elongated tubular body and has a substantially equal diameter along its longitudinal axis, and a vertebra introducer stylet inserted in the vertebra access cannula having an elongated cylindrical body, a proximal end and distal end and a longitudinal axis along the elongated cylindrical body, wherein the elongated cylindrical body has a substantially equal diameter along its longitudinal axis, wherein the diameter of the elongated cylindrical body is less than the diameter of the inner lumen of the vertebra access cannula but nearly equal to the diameter of the inner lumen of the vertebra access cannula such that the vertebra introducer stylet fills the inner lumen of the vertebra introducer cannula but may be retracted through the inner lumen, and wherein the distal end terminates in a tip, wherein the tip is arranged eccentrically to the longitudinal axis of the elongated cylindrical body, wherein the tip is formed by three cut surfaces, wherein a first cut surface is larger than the second and third cut surfaces, wherein the second and third cut surfaces are identical in size.

Any of the above aspects, wherein the substantially equal diameter of the elongated cylindrical body of the vertebra introducer stylet has length of 3.40 mm to 3.60 mm, preferably a length of 3.45 mm to 3.55 mm, more preferably a length of 3.50 mm.

Any of the above aspects, wherein the elongated cylindrical body of the vertebra introducer stylet has a length from the tip to the proximal end of 173.40 mm to 174.60 mm, preferably a length of 173.70 mm to 174.30 mm, more preferably a length of 174 mm.

Any of the above aspects, wherein the vertebra introducer stylet comprise a handle at the proximal end, wherein the elongated cylindrical body of the vertebra introducer stylet has a length including the handle from the tip to the handle of 177.60 mm to 179.60 mm, preferably a length of 178.10 mm to 179.10 mm, more preferably a length of 178.60 mm.

Any of the above aspects, wherein the proximal end of the elongated cylindrical body of the vertebra introducer stylet is arranged in a stopper device, wherein the elongated cylindrical body of the vertebra introducer stylet has a length without the stopper device from the tip to the stopper device of 152.00 mm to 154.00 mm, preferably a length of 152.50 mm to 153.50 mm, more preferably a length of 153.00 mm.

Any of the above aspects, wherein the vertebra introducer stylet when arranged in the vertebra access cannula the tip of the vertebra introducer stylet protrudes 9.00 to 11.00 mm, preferably 9.50 to 10.50, more preferably 10.00 mm from the distal end of the vertebra access cannula.

Any of the above aspects, wherein the first cut surface of the tip of the vertebra introducer stylet is arranged in an angle of 19 to 29° to the longitudinal axis of the elongated cylindrical body, preferably in an angle of 23 to 25°, more preferably in an angle of 24°.

Any of the above aspects, wherein the first cut surface of the tip of the vertebra introducer stylet has a length from the tip to an opposite end of the first cut surface of the tip of 7.18 mm to 7.78 mm, preferably a length of 7.33 mm to 7.63 mm, more preferably a length of 7.48 mm.

Any of the above aspects, wherein the second and third cut surfaces of the tip of the vertebra introducer stylet are arranged in an angle of 17 to 27° to the longitudinal axis of the elongated cylindrical body, preferably in an angle of 21 to 23°, more preferably in an angle of 22°.

Any of the above aspects, wherein the tip of the vertebra introducer stylet is formed by three bevel wherein a first bevel is shorter than the second and third bevel, wherein the second and third bevel are identical in size, and wherein the first bevel is arranged between the second and third cut surfaces and wherein the first bevel is arranged in an angle of 35 to 45° from the tip to the longitudinal axis of the elongated cylindrical body, preferably in an angle of 38 to 42°, more preferably in an angle of 40°.

Any of the above aspects, wherein the second and third bevel have a length of 1.85 mm to 2.45 mm, preferably a length of 2.00 mm to 2.30 mm, more preferably a length of 2.15 mm.

A kit for treating fractured vertebrae of patient in need thereof, the kit comprising:

a percutaneous access path providing device for providing a percutaneous access path to the vertebral body, wherein the percutaneous access path providing device comprising a vertebra access cannula having an elongated tubular body with an inner lumen, a proximal end and distal end and a longitudinal axis along the elongated tubular body, wherein the inner lumen extending the length of the elongated tubular body and has a substantially equal diameter along its longitudinal axis, and a vertebra introducer stylet inserted in the vertebra access cannula having an elongated cylindrical body, a proximal end and distal end and a longitudinal axis along the elongated cylindrical body, wherein the elongated cylindrical body has a substantially equal diameter along its longitudinal axis, wherein the diameter of the elongated cylindrical body is less than the diameter of the inner lumen of the vertebra access cannula but nearly equal to the diameter of the inner lumen of the vertebra access cannula such that the vertebra introducer stylet fills the inner lumen of the vertebra access cannula but may be retracted through the inner lumen, and wherein the distal end terminates in a tip, wherein the tip is arranged eccentrically to the longitudinal axis of the elongated cylindrical body, wherein the tip is formed by three cut surfaces, wherein a first cut surface is larger than the second and third cut surfaces, wherein the second and third cut surfaces are identical in size, a balloon catheter shaped and dimensioned to be insertable into the vertebra access cannula to create a void in the cancellous bone, wherein the balloon catheter has a first end and a second end, the first end being adapted for getting inserted into the vertebra access cannula and the second end being adapted for remaining outside of the vertebra access cannula, the first end comprising an expandable balloon structure adapted to undergo expansion in the cancellous bone structure to a predetermined size and shape, the second end comprising adaptor means for connecting the balloon catheter to a fluid providing means, fluid providing means, filler device shaped and dimensioned to be insertable into the vertebra access cannula comprising
- a filler cannula device for filling with bone cement, and
- a filler tamping device shaped and dimensioned to be insertable into the filler cannula device for forcing the bone cement from the filler cannula device into the void of the cancellous bone.

Any of the above aspects, wherein the substantially equal diameter of the elongated cylindrical body of the vertebra introducer stylet of the percutaneous access path providing device has length of 3.40 mm to 3.60 mm, preferably a length of 3.45 mm to 3.55 mm, more preferably a length of 3.50 mm.

Any of the above aspects, wherein the elongated cylindrical body of the vertebra introducer stylet of the percutaneous access path providing device has a length from the tip to the proximal end of 173.40 mm to 174.60 mm, preferably a length of 173.70 mm to 174.30 mm, more preferably a length of 174 mm.

Any of the above aspects, wherein the vertebra introducer stylet of the percutaneous access path providing device comprise a handle at the proximal end, wherein the elongated cylindrical body of the vertebra introducer stylet has a length including the handle from the tip to the handle of 177.60 mm to 179.60 mm, preferably a length of 178.10 mm to 179.10 mm, more preferably a length of 178.60 mm.

Any of the above aspects, wherein the proximal end of the elongated cylindrical body of the vertebra introducer stylet of the percutaneous access path providing device is arranged in a stopper device, wherein the elongated cylindrical body of the vertebra introducer stylet has a length without the stopper device from the tip to the stopper device of 152.00 mm to 154.00 mm, preferably a length of 152.50 mm to 153.50 mm, more preferably a length of 153.00 mm.

Any of the above aspects, wherein the vertebra introducer stylet when arranged in the vertebra access cannula the tip of the vertebra introducer stylet protrudes 9.00 to 11.00 mm, preferably 9.50 to 10.50, more preferably 10.00 mm from the distal end of the vertebra access cannula.

Any of the above aspects, wherein the first cut surface of the tip of the vertebra introducer stylet of the percutaneous access path providing device is arranged in an angle of 19 to 29° to the longitudinal axis of the elongated cylindrical body, preferably in an angle of 23 to 25°, more preferably in an angle of 24°.

Any of the above aspects, wherein the first cut surface of the tip of the vertebra introducer stylet of the percutaneous access path providing device has a length from the tip to an opposite end of the first cut surface of the tip of 7.18 mm to 7.78 mm, preferably a length of 7.33 mm to 7.63 mm, more preferably a length of 7.48 mm.

Any of the above aspects, wherein the second and third cut surfaces of the tip of the vertebra introducer stylet of the percutaneous access path providing device are arranged in an angle of 17 to 27° to the longitudinal axis of the elongated cylindrical body, preferably in an angle of 21 to 23°, more preferably in an angle of 22°.

Any of the above aspects, wherein the tip of the vertebra introducer stylet of the percutaneous access path providing device is formed by three bevel wherein a first bevel is shorter than the second and third bevel, wherein the second and third bevel are identical in size, and wherein the first bevel is arranged between the second and third cut surfaces and wherein the first bevel is arranged in an angle of 35 to 45° from the tip to the longitudinal axis of the elongated cylindrical body, preferably in an angle of 38 to 42°, more preferably in an angle of 40°.

Any of the above aspects, wherein the second and third bevel have a length of 1.85 mm to 2.45 mm, preferably a length of 2.00 mm to 2.30 mm, more preferably a length of 2.15 mm.

Any of the above aspects, wherein the balloon catheter comprises two expandable structures, a first expandable structure and a second expandable structure, wherein the first expandable structure and the second expandable structure are spaced from one another and wherein the first and the second expandable structure can be inflated and deflated independently from one another to create a desired void in the cancellous bone another.

Any of the above aspects, wherein the fluid providing means comprising an inflation device.

Any of the above aspects, wherein the kit further comprises a cannula plug device shaped and dimensioned to be insertable into the vertebra access cannula for preventing inadvertent blood drainage through the vertebra access cannula or for preventing a cement leakage through the vertebra access cannula.

Any of the above aspects, wherein the kit further comprises a second vertebra access cannula for providing a second percutaneous access path to the vertebral body.

Any of the above aspects, wherein the kit further comprises a vertebra biopsy device for taking a biopsy sample from the inner cancellous bone.

Any of the above aspects, wherein the kit further comprises a bone drill for generating a path through the outer cortical bone structure into the inner cancellous bone structure.

Any of the above aspects, wherein the kit further comprises bone cement.

Any of the above aspects, wherein the kit further comprises a vacuum syringe

What is claimed is:

1. A method for treating fractured vertebrae of a patient in need thereof, the method comprising the following consecutive steps:
   a) selecting a vertebral body for treatment, the vertebral body comprising a fracture and having an outer cortical bone structure, an inner cancellous bone structure surrounded by the outer cortical bone structure, and two pedicles,
   b) incising a skin portion covering the vertebral body for treatment to provide for an incision in the skin portion,
   c) introducing a percutaneous access path providing device into the incision and advancing the percutaneous access path providing device to the vertebral body for providing a percutaneous access path to the vertebral body, wherein the percutaneous access path providing device comprising
       a vertebra access cannula having an elongated tubular body with an inner lumen, a proximal end and distal end and a longitudinal axis along the elongated tubular body, wherein the inner lumen extending the length of the elongated tubular body and has a substantially equal diameter along its longitudinal axis, and a vertebra introducer stylet inserted in the vertebra access cannula having an elongated cylindrical body, a proximal end and distal end and a longitudinal axis along the elongated cylindrical body, wherein the elongated cylindrical body has a substantially equal diameter along its longitudinal axis, wherein the diameter of the elongated cylindrical body is less than the diameter of the inner lumen of the vertebra access cannula but nearly equal to the diameter of the inner lumen of the vertebra access cannula such that the vertebra introducer stylet fills the inner lumen of the vertebra access cannula but may be retracted through the inner lumen, and wherein the distal end terminates in a tip, wherein the tip is arranged eccentrically to the longitudinal axis of the elongated cylindrical body, wherein the tip is formed by three cut surfaces, wherein a first cut surface is larger than the second and third cut surfaces, wherein the second and third cut surfaces are identical in size, d) removing the vertebra introducer stylet from the vertebra access cannula, e1) advancing a bone drill device through the vertebra access cannula and operating such that a path is generated through the outer cortical bone structure into the inner cancellous bone structure, and e2) removing the bone drill device from the vertebra access cannula, e) introducing, into the vertebra access cannula, a balloon catheter shaped and dimensioned to be insertable into the vertebra access cannula, and forwarding such to the cancellous bone; the balloon catheter having a first end and a second end, the first end being adapted for getting inserted into the vertebra access cannula and the second end being adapted for remaining outside of the vertebra access cannula, the first end comprising two expandable balloon structures, a first expandable structure and a second expandable structure, adapted to undergo expansion in the cancellous bone structure to a predetermined size and shape, wherein the first expandable structure and the second expandable structure are spaced from one another and wherein the first and the second expandable structures can be inflated and deflated independently from one another to create a desired void in the cancellous bone; and the second end of the balloon catheter comprising an adaptor configured to connect the balloon catheter to a fluid providing means, f) expanding the expandable structures in the cancellous bone structure to a predetermined shape and size to create a void in the cancellous bone, by providing fluid into the expandable structure via the fluid providing means, g) unexpanding the expandable structures and removing the balloon catheter from the vertebra access cannula, h) filling, outside of the vertebra access cannula, a filler cannula device with bone cement, i) placing the filler cannula device filled with bone cement into the vertebra access cannula and advancing the filler cannula device to the void in the cancellous bone, j) inserting, into the filler cannula device placed within the vertebra access cannula, a filler tamping device and advancing the filler tamping device within the filler cannula device, thereby forcing the bone cement from the filler cannula device into the void, the filler cannula device and the filler tamping device, nested together, forming a filler device, and k) removing the filler cannula device form the vertebra access cannula and removing the vertebra access cannula from the subcutaneous access path, and l) closing the incision.

2. The method of claim 1, wherein the steps are performed on each of the pedicle of the vertebral body with a separate set of devices, respectively, therefore in step b) two incisions in the skin portion are provided, and after step d) the method comprises the further consecutive steps of:

d1) introducing, outside of the first vertebra access cannula, the vertebra introducer stylet into a second vertebra access cannula, wherein the second vertebra access cannula is identically structured as the first vertebra access cannula, wherein the second vertebra access cannula and the vertebra introducer stylet, nested together, forming a second percutaneous access path providing device, d2) introducing the second percutaneous access path providing device into the second incision and advancing the second percutaneous access path providing device to the vertebral body for providing a second percutaneous access path to the vertebral body, and d3) removing the vertebra introducer stylet of the second vertebra access cannula.

3. The method of claim 1, wherein the first cut surface of the tip of the vertebra introducer stylet is arranged in an angle of 19 to 29° to the longitudinal axis of the elongated cylindrical body.

4. The method of claim 1, wherein the first cut surface of the tip of the vertebra introducer stylet has a length from the tip to an opposite end of the first cut surface of the tip of 7.18 mm to 7.78 mm.

5. The method of claim 1, wherein the second and third cut surfaces of the tip of the vertebra introducer stylet are arranged in an angle of 17 to 27° to the longitudinal axis of the elongated cylindrical body.

6. The method of claim 1, wherein the tip of the vertebra introducer stylet is formed by three bevel wherein a first bevel is shorter than the second and third bevel, wherein the second and third bevel are identical in size, and wherein the first bevel is arranged between the second and third cut surfaces and wherein the first bevel is arranged in an angle of 35 to 45° from the tip to the longitudinal axis of the elongated cylindrical body.

7. The method of claim 6, wherein the second and third bevel have a length of 1.85 mm to 2.45 mm.

8. A kit for treating fractured vertebrae of patient in need thereof, the kit comprising:

a percutaneous access path providing device for providing a percutaneous access path to the vertebral body, wherein the percutaneous access path providing device comprising a vertebra access cannula having an elongated tubular body with an inner lumen, a proximal end and distal end and a longitudinal axis along the elongated tubular body, wherein the inner lumen extending the length of the elongated tubular body and has a substantially equal diameter along its longitudinal axis, and a vertebra introducer stylet inserted in the vertebra access cannula having an elongated cylindrical body, a proximal end and distal end and a longitudinal axis along the elongated cylindrical body, wherein the elongated cylindrical body has a substantially equal diameter along its longitudinal axis, wherein the diameter of the elongated cylindrical body is less than the diameter of the inner lumen of the vertebra access cannula but nearly equal to the diameter of the inner lumen of the vertebra access cannula such that the vertebra introducer stylet fills the inner lumen of the vertebra access cannula but may be retracted through the inner lumen, and wherein the distal end terminates in a tip, wherein the tip is arranged eccentrically to the longitudinal axis of the elongated cylindrical body, wherein the tip is non-cannulated and formed by three solid cut surfaces, wherein a first cut surface is larger than the second and third cut surfaces, wherein the second and third cut surfaces are identical in size, a balloon catheter shaped and dimensioned to be insertable into the vertebra access cannula to create a void in the cancellous bone, wherein the balloon catheter has a first end and a second end, the first end being adapted for getting inserted into the vertebra access cannula and the second end being adapted for remaining outside of the vertebra access cannula, the first end comprising two expandable balloon structures, a first expandable structure and a second expandable structure, adapted to undergo expansion in the cancellous bone structure to a predetermined size and shape, wherein the first expandable structure and the second expandable structure are spaced from one another and wherein the first and the second expandable structure can be inflated and deflated independently from one another to create a desired void in the cancellous bone; and the second end of the balloon catheter comprising an adaptor configured to connect the balloon catheter to a fluid providing means, fluid providing means, filler device shaped and dimensioned to be insertable into the vertebra access cannula comprising
- a filler cannula device for filling with bone cement, and
- a filler tamping device shaped and dimensioned to be insertable into the filler cannula device for forcing the bone cement from the filler cannula device into the void of the cancellous bone.

9. The kit of claim 8 wherein the vertebra introducer stylet when arranged in the vertebra access cannula the tip of the vertebra introducer stylet protrudes 9.00 to 11.00 mm from the distal end of the vertebra access cannula.

10. The kit of claim 8, wherein the first cut surface of the tip of the vertebra introducer stylet of the percutaneous access path providing device is arranged in an angle of 19 to 29° to the longitudinal axis of the elongated cylindrical body.

11. The kit of claim 8, wherein the first cut surface of the tip of the vertebra introducer stylet of the percutaneous access path providing device has a length from the tip to an opposite end of the first cut surface of the tip of 7.18 mm to 7.78 mm.

12. The kit of claim 8, wherein the second and third cut surfaces of the tip of the vertebra introducer stylet of the percutaneous access path providing device are arranged in an angle of 17 to 27° to the longitudinal axis of the elongated cylindrical body.

13. The kit of claim 8, wherein the tip of the vertebra introducer stylet of the percutaneous access path providing device is formed by three bevel wherein a first bevel is shorter than the second and third bevel, wherein the second and third bevel are identical in size, and wherein the first bevel is arranged between the second and third cut surfaces and wherein the first bevel is arranged in an angle of 35 to 45° from the tip to the longitudinal axis of the elongated cylindrical body.

14. The kit of claim 13, wherein the second and third bevel have a length of 1.85 mm to 2.45 mm.

15. The kit of claim 8, wherein the kit further comprises one or more of the following: a cannula plug device shaped and dimensioned to be insertable into the vertebra access cannula for preventing inadvertent blood drainage through the vertebra access cannula or for preventing a cement leakage through the vertebra access cannula; a second vertebra access cannula for providing a second percutaneous access path to the vertebral body; a vertebra biopsy device for taking a biopsy sample from the inner cancellous bone; a bone drill for generating a path through the outer cortical bone structure into the inner cancellous bone structure; bone cement; and a vacuum syringe.

* * * * *